(12) United States Patent
Northrop

(10) Patent No.: US 9,227,037 B2
(45) Date of Patent: Jan. 5, 2016

(54) CUT TUBULAR MEMBERS FOR A MEDICAL DEVICE AND METHODS FOR MAKING AND USING THE SAME

(71) Applicant: BOSTON SCIENTIFIC SCIMED, INC., Maple Grove, MN (US)

(72) Inventor: Clay Northrop, Salt Lake City, UT (US)

(73) Assignee: BOSTON SCIENTIFIC SCIMED, INC., Maple Grove, MN (US)

( * ) Notice: Subject to any disclaimer, the term of this patent is extended or adjusted under 35 U.S.C. 154(b) by 26 days.

(21) Appl. No.: 13/915,449

(22) Filed: Jun. 11, 2013

(65) Prior Publication Data

US 2013/0267913 A1    Oct. 10, 2013

Related U.S. Application Data

(63) Continuation of application No. 11/969,212, filed on Jan. 3, 2008, now Pat. No. 8,460,213.

(51) Int. Cl.
*A61M 25/09* (2006.01)
*A61M 25/00* (2006.01)
*A61B 1/00* (2006.01)
*A61B 1/005* (2006.01)

(52) U.S. Cl.
CPC .......... *A61M 25/0021* (2013.01); *A61B 1/0011* (2013.01); *A61B 1/00071* (2013.01); *A61M 25/0013* (2013.01); *A61M 25/0054* (2013.01); *A61M 25/09* (2013.01); *A61B 1/0055* (2013.01); *A61M 2025/0059* (2013.01); *A61M 2025/0915* (2013.01); *A61M 2025/09091* (2013.01); *A61M 2025/09108* (2013.01); *Y10T 83/0524* (2015.04)

(58) Field of Classification Search
USPC .......................................... 600/585; 604/523
See application file for complete search history.

(56) References Cited

U.S. PATENT DOCUMENTS

| | | |
|---|---|---|
| 4,547,193 A | 10/1985 | Rydell |
| 4,753,238 A | 6/1988 | Gaiser et al. |
| 4,795,439 A | 1/1989 | Guest et al. |
| 4,998,923 A | 3/1991 | Samson et al. |
| 5,095,915 A | 3/1992 | Engelson et al. |
| 5,106,455 A | 4/1992 | Jacobsen et al. |
| 5,228,441 A | 7/1993 | Lundquist |
| 5,238,004 A | 8/1993 | Sahatjian et al. |
| 5,315,996 A | 5/1994 | Lundquist |
| 5,322,064 A | 6/1994 | Lundquist |
| 5,328,472 A | 7/1994 | Steinke et al. |
| 5,329,923 A | 7/1994 | Lundquist |
| 5,334,145 A | 8/1994 | Lundquist et al. |
| 5,372,144 A | 12/1994 | Mortier et al. |
| 5,437,288 A | 8/1995 | Schwartz et al. |
| 5,477,856 A | 12/1995 | Lundquist |
| 5,480,551 A | 1/1996 | Chudoba et al. |
| 5,507,751 A | 4/1996 | Goode et al. |

(Continued)

FOREIGN PATENT DOCUMENTS

| | | |
|---|---|---|
| EP | 1144039 B1 | 12/2005 |
| EP | 1457224 B1 | 7/2008 |

(Continued)

*Primary Examiner* — Sean Dougherty
(74) *Attorney, Agent, or Firm* — Seager, Tufte & Wickhem LLP

(57) ABSTRACT

Medical devices and methods for making and using the same. An example medical devices includes a core member and a tubular member disposed over a portion of the core member. The tubular member has a plurality of slots formed therein.

9 Claims, 14 Drawing Sheets

(56) References Cited

U.S. PATENT DOCUMENTS

| | | | |
|---|---|---|---|
| 5,507,766 A | 4/1996 | Kugo et al. | |
| 5,569,197 A | 10/1996 | Helmus et al. | |
| 5,573,520 A | 11/1996 | Schwartz et al. | |
| 5,695,506 A | 12/1997 | Pike et al. | |
| 5,741,429 A | 4/1998 | Donadio et al. | |
| 5,772,609 A | 6/1998 | Nguyen et al. | |
| 5,772,669 A | 6/1998 | Vrba et al. | |
| 5,788,707 A | 8/1998 | Del Toro et al. | |
| 5,833,632 A * | 11/1998 | Jacobsen et al. | 600/585 |
| 5,902,290 A | 5/1999 | Peacock, III et al. | |
| 5,968,069 A | 10/1999 | Dusbabek et al. | |
| 5,979,856 A | 11/1999 | Hsu | |
| 6,001,068 A | 12/1999 | Uchino et al. | |
| 6,004,279 A | 12/1999 | Crowley et al. | |
| 6,014,919 A | 1/2000 | Jacobsen et al. | |
| 6,017,319 A | 1/2000 | Jacobsen et al. | |
| 6,048,339 A | 4/2000 | Zirps et al. | |
| 6,068,635 A | 5/2000 | Gianotti | |
| 6,077,295 A | 6/2000 | Limon et al. | |
| 6,096,045 A | 8/2000 | Del Toro et al. | |
| 6,102,932 A | 8/2000 | Kurz et al. | |
| 6,106,455 A | 8/2000 | Kan | |
| 6,123,712 A | 9/2000 | Di Caprio et al. | |
| 6,139,510 A | 10/2000 | Palermo et al. | |
| 6,168,617 B1 | 1/2001 | Blaeser et al. | |
| 6,174,327 B1 | 1/2001 | Mertens et al. | |
| 6,203,558 B1 | 3/2001 | Dusbabek et al. | |
| 6,241,758 B1 | 6/2001 | Cox | |
| 6,245,095 B1 | 6/2001 | Dobak, III et al. | |
| 6,260,458 B1 | 7/2001 | Jacobsen et al. | |
| 6,287,291 B1 | 9/2001 | Bigus et al. | |
| 6,287,315 B1 | 9/2001 | Wijeratne et al. | |
| 6,302,893 B1 | 10/2001 | Limon et al. | |
| 6,325,814 B1 | 12/2001 | Euteneuer et al. | |
| 6,342,066 B1 | 1/2002 | Toro et al. | |
| 6,371,962 B1 | 4/2002 | Ellis et al. | |
| 6,398,802 B1 | 6/2002 | Yee | |
| 6,428,489 B1 | 8/2002 | Jacobsen et al. | |
| 6,428,566 B1 | 8/2002 | Holt | |
| 6,431,039 B1 | 8/2002 | Jacobsen et al. | |
| 6,436,090 B1 | 8/2002 | Sanchez et al. | |
| 6,440,088 B1 | 8/2002 | Jacobsen et al. | |
| 6,508,803 B1 | 1/2003 | Horikawa et al. | |
| 6,514,280 B1 | 2/2003 | Gilson | |
| 6,517,569 B2 | 2/2003 | Mikus et al. | |
| 6,530,947 B1 | 3/2003 | Euteneuer et al. | |
| 6,533,805 B1 | 3/2003 | Jervis | |
| 6,562,064 B1 | 5/2003 | deBeer | |
| 6,576,008 B2 | 6/2003 | Devonec et al. | |
| 6,579,246 B2 | 6/2003 | Jacobsen et al. | |
| 6,592,549 B2 | 7/2003 | Gerdts et al. | |
| 6,592,568 B2 | 7/2003 | Campbell | |
| 6,592,569 B2 | 7/2003 | Bigus et al. | |
| 6,602,280 B2 | 8/2003 | Chobotov | |
| 6,607,555 B2 | 8/2003 | Patterson et al. | |
| 6,610,046 B1 | 8/2003 | Usami et al. | |
| 6,623,491 B2 | 9/2003 | Thompson | |
| 6,629,981 B2 | 10/2003 | Bui et al. | |
| 6,652,508 B2 | 11/2003 | Griffin et al. | |
| 6,660,031 B2 | 12/2003 | Tran et al. | |
| 6,669,716 B1 | 12/2003 | Gilson et al. | |
| 6,676,666 B2 | 1/2004 | Vrba et al. | |
| 6,699,274 B2 | 3/2004 | Stinson | |
| 6,702,802 B1 | 3/2004 | Hancock et al. | |
| 6,712,827 B2 | 3/2004 | Ellis et al. | |
| 6,723,071 B2 | 4/2004 | Gerdts et al. | |
| 6,726,714 B2 | 4/2004 | DiCaprio et al. | |
| 6,743,210 B2 | 6/2004 | Hart et al. | |
| 6,766,720 B1 | 7/2004 | Jacobsen et al. | |
| 6,773,446 B1 | 8/2004 | Dwyer et al. | |
| 6,786,876 B2 | 9/2004 | Cox | |
| 6,802,849 B2 | 10/2004 | Blaeser et al. | |
| 6,918,882 B2 | 7/2005 | Skujins et al. | |
| 7,001,369 B2 | 2/2006 | Griffin et al. | |
| 7,074,197 B2 | 7/2006 | Reynolds et al. | |
| 7,914,467 B2 * | 3/2011 | Layman et al. | 600/585 |
| 8,092,444 B2 * | 1/2012 | Lentz et al. | 604/525 |
| 8,292,827 B2 * | 10/2012 | Musbach et al. | 600/585 |
| 8,376,961 B2 * | 2/2013 | Layman et al. | 600/585 |
| 8,419,658 B2 * | 4/2013 | Eskuri | 600/585 |
| 8,460,213 B2 * | 6/2013 | Northrop | 600/585 |
| 8,551,021 B2 * | 10/2013 | Voeller et al. | 600/585 |
| 8,556,914 B2 * | 10/2013 | Vrba | 606/127 |
| 8,585,643 B2 * | 11/2013 | Vo et al. | 604/103.09 |
| 8,821,477 B2 * | 9/2014 | Northrop et al. | 604/523 |
| 2003/0009208 A1 | 1/2003 | Snyder et al. | |
| 2003/0069522 A1 | 4/2003 | Jacobsen et al. | |
| 2003/0093059 A1 | 5/2003 | Griffin et al. | |
| 2003/0125013 A1 | 7/2003 | Eidenschink | |
| 2004/0111044 A1 * | 6/2004 | Davis et al. | 600/585 |
| 2004/0167437 A1 | 8/2004 | Sharrow et al. | |
| 2004/0167441 A1 | 8/2004 | Reynolds et al. | |
| 2004/0181174 A2 * | 9/2004 | Davis et al. | 600/585 |
| 2005/0065456 A1 | 3/2005 | Eskuri | |
| 2005/0187602 A1 | 8/2005 | Eidenschink | |
| 2005/0234499 A1 | 10/2005 | Olson et al. | |
| 2006/0189896 A1 | 8/2006 | Davis et al. | |
| 2007/0083132 A1 | 4/2007 | Sharrow | |
| 2007/0135763 A1 * | 6/2007 | Musbach et al. | 604/96.01 |

FOREIGN PATENT DOCUMENTS

| | | |
|---|---|---|
| WO | 9524236 A1 | 9/1995 |
| WO | 9744086 A1 | 11/1997 |
| WO | 9810694 A3 | 7/1998 |
| WO | 0025849 A1 | 5/2000 |
| WO | 03004086 A3 | 11/2003 |

* cited by examiner

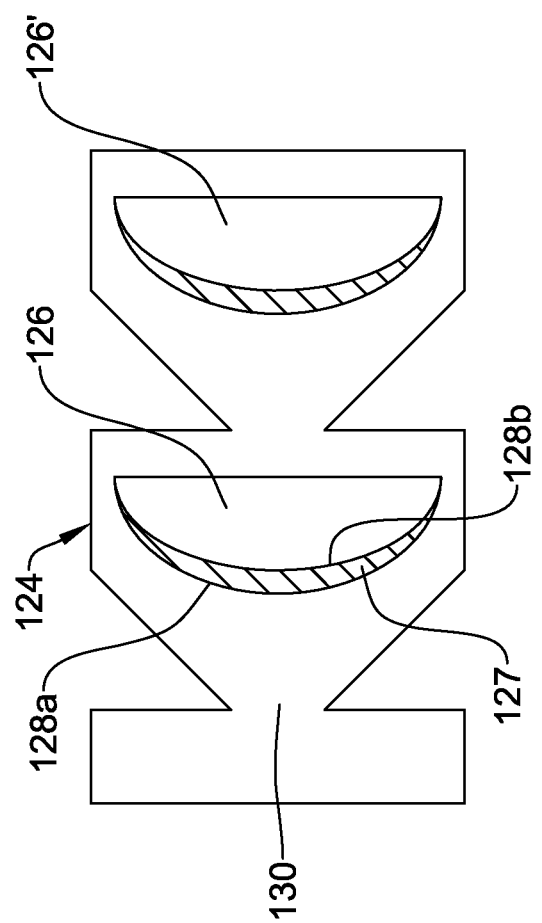
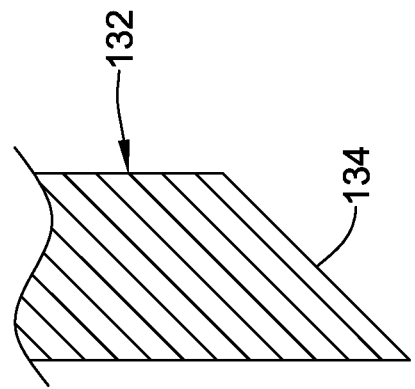
Figure 5
Figure 6

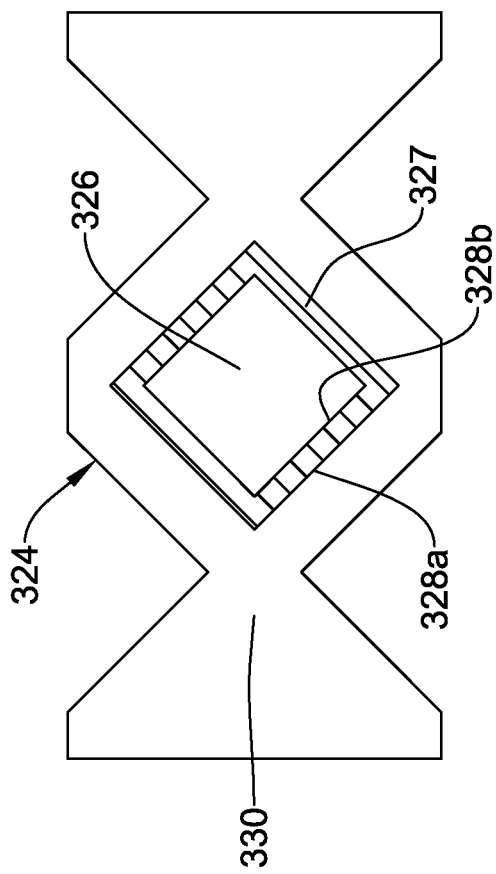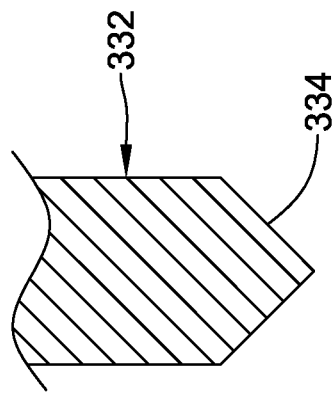

CUT TUBULAR MEMBERS FOR A MEDICAL DEVICE AND METHODS FOR MAKING AND USING THE SAME

CROSS-REFERENCE TO RELATED APPLICATIONS

This application is a continuation of U.S. application Ser. No. 11/969,212, filed Jan. 3, 2008, now U.S. Pat. No. 8,460,213, under 35 U.S.C. §119(e), the entire disclosure of which is incorporated herein by reference.

FIELD OF THE INVENTION

The present invention pertains to intracorporal medical devices, for example, intravascular guidewires, catheters, and the like as well as improved methods for manufacturing medical devices. More particularly, the invention relates to medical devices including a tubular member having a plurality of slots formed therein.

BACKGROUND

A wide variety of intracorporeal medical devices have been developed for medical use, for example, intravascular use. Some of these devices include guidewires, catheters, and the like. Of the known medical devices, each has certain advantages and disadvantages. There is an ongoing need to provide alternative medical devices as well as alternative methods for manufacturing and using medical devices.

BRIEF SUMMARY

The invention provides design, material, and manufacturing method alternatives for medical devices. An example medical device includes a tubular member having a plurality of slots formed therein. The slots can be arranged and/or configured in a number of different ways. Some of these and other features and characteristics of the inventive devices and methods are described in more detail below.

The above summary of some embodiments is not intended to describe each disclosed embodiment or every implementation of the present invention. The Figures, and Detailed Description, which follow, more particularly exemplify these embodiments.

BRIEF DESCRIPTION OF THE DRAWINGS

The invention may be more completely understood in consideration of the following detailed description of various embodiments of the invention in connection with the accompanying drawings, in which:

FIG. 5 illustrates a portion of another example tubular member;

FIG. 6 illustrates a portion of another example cutting blade;

FIG. 8 illustrates a portion of another example tubular member;

FIG. 9 illustrates a portion of another example cutting blade;

Figure 1:
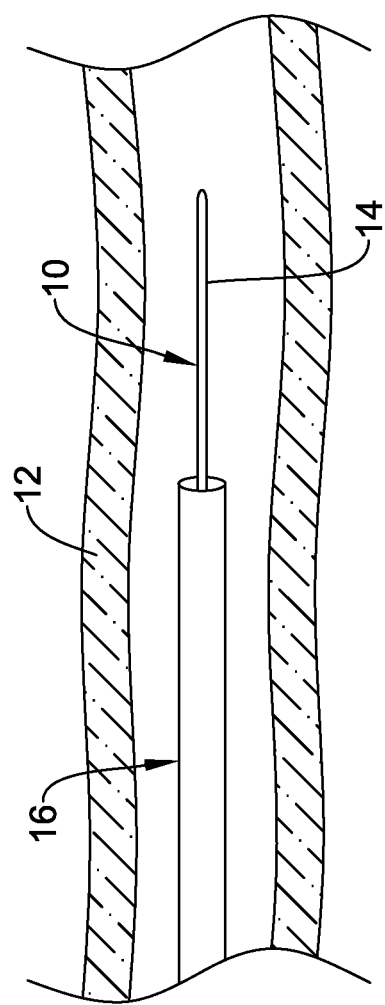
FIG. 1 is a plan view of an example medical device disposed in a blood vessel.

While the invention is amenable to various modifications and alternative forms, specifics thereof have been shown by way of example in the drawings and will be described in detail. It should be understood, however, that the intention is not to limit the invention to the particular embodiments described. On the contrary, the intention is to cover all modifications, equivalents, and alternatives falling within the spirit and scope of the invention.

DETAILED DESCRIPTION

For the following defined terms, these definitions shall be applied, unless a different definition is given in the claims or elsewhere in this specification.

All numeric values are herein assumed to be modified by the term "about," whether or not explicitly indicated. The term "about" generally refers to a range of numbers that one of skill in the art would consider equivalent to the recited value (i.e., having the same function or result). In many instances, the terms "about" may include numbers that are rounded to the nearest significant figure.

The recitation of numerical ranges by endpoints includes all numbers within that range (e.g. 1 to 5 includes 1, 1.5, 2, 2.75, 3, 3.80, 4, and 5).

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise.

The following detailed description should be read with reference to the drawings in which similar elements in different drawings are numbered the same. The drawings, which are not necessarily to scale, depict illustrative embodiments and are not intended to limit the scope of the invention.

FIG. 1 is a plan view of an example medical device 10, for example a guidewire, disposed in a blood vessel 12. Guidewire 10 may include a distal section 14 that may be generally configured for use within the anatomy of a patient. Guidewire 10 may be used for intravascular procedures according to common practice and procedure. For example, guidewire 10 may be used in conjunction with another medical device 16, which may take the form of a catheter, to treat and/or diagnose a medical condition. Of course, numerous other uses are known amongst clinicians for guidewires and other similarly configured medical devices.

Figure 2:
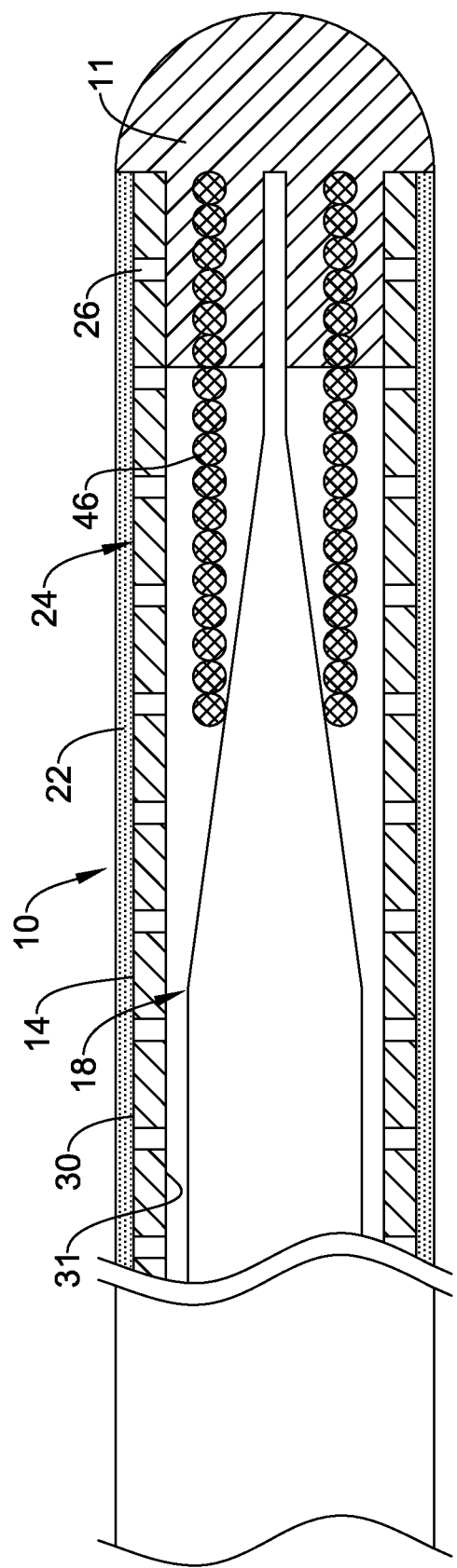
FIG. 2 is a partially cut-away side view of an example medical device.

Turning now to FIG. 2, distal section 14 of guidewire 10 is illustrated. Here it can be seen that guidewire 10 may include a core wire 18 and a tubular member 24 disposed over at least a portion of core wire 18. In some embodiments, core wire 18 may extend to the distal end of tubular member 24. In other embodiments, tubular member 24 may extend distally beyond the distal end of core wire 18. A sheath or covering 22 may be disposed over portions or all of core wire 18 and/or tubular member 24 that may define a generally smooth outer surface for guidewire 10. In other embodiments, however, such a sheath or covering 22 may be absent from a portion of all of guidewire 10, such that tubular member 24 and/or core wire 18 may form the outer surface. A coil 46 may be disposed adjacent to core wire 18 and/or tubular member 24. In FIG. 2, the sheath or covering 22 is partially cut away to show a side view of core wire 18 and tubular member 24. A rounded or generally atraumatic distal tip 11 can be formed at the distal end of guidewire 10. Core wire 18 may extend to and/or into distal tip 11, or may end proximally thereof. In some embodiments, tubular member 24 is attached to core wire 18. For example, tubular member 24 and core wire 18 can be attached at the proximal end of tubular member 24, the distal end of tubular member 24, both, and/or at any suitable position therebetween. Some additional description regarding the attachment of core wires and tubular members can be found in U.S. Patent Pub. No. 2004/0181174-A2, the entire contents of which are herein incorporated by reference.

Figure 2A:
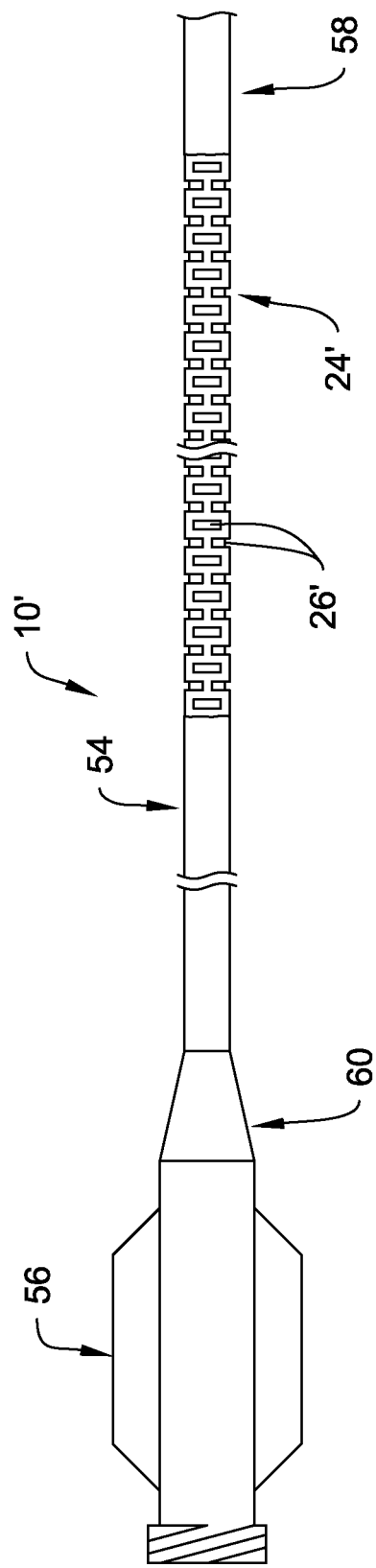
FIG. 2A is a partially cut-away side view of another example medical device.
Figure 4:
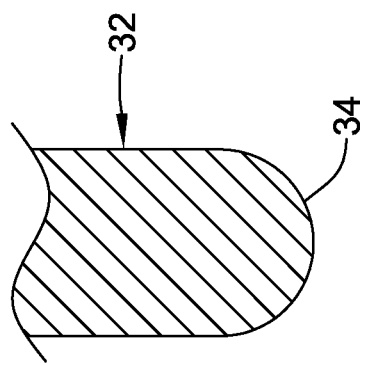
FIG. 4 illustrates a portion of an example cutting blade.

It should be noted that although some of the discussion herein is directed to embodiments where medical device 10 is a guidewire, this is not intended to be limiting. It can be appreciated that numerous alternative embodiments are contemplated where device 10 is another device such as a catheter (including guide catheters, balloon catheters, etc.), endoscopic device, laparoscopic device, and the like or any other suitable guiding, diagnosing, or treating device that be suitable for use at essentially any location and/or body lumen within a patient. For example, FIG. 2A depicts another example medical device 10' as a catheter having a catheter shaft 54. The proximal end of shaft 54 may include a proximal hub 56. Hub 56 may include a strain relief 60. The distal end of shaft 54 may include a distal tip region 58 which may take any number of forms. Catheter shaft 54 may include tubular member 24', which may be similar to other tubular members disclosed herein including tubular member 24. A plurality of slots 26' may be formed in tubular member 24'. Slots 26' may be similar to slots 26 (described below) or any other slots described herein. Tubular member 24' may extend along any portion or all of catheter shaft 54. Catheter 10' may also include any of the features described in U.S. Pat. No. 7,001, 369, the entire disclosure of which is herein incorporated by reference.

Turning back now to FIG. 2, as indicated above tubular member 24 may include a plurality of slots 26 formed therein that extend, for example, at least part of the way between the outer surface 30 and the inner surface 31 of tubular member 24. Slots 26 may be micromachined or otherwise created in tubular member 24, and may be configured to make tubular member 24 more flexible in bending. It is worth noting that, to the extent applicable, the methods for forming slots 26 can include, for example, any of the appropriate micromachining methods and other cutting methods disclosed in U.S. Pat. Publication Nos. US 2003/0069522 and US 2004/0181174 A2, and/or U.S. Pat. Nos. 6,766,720 and 6,579,246, the entire disclosures of which are herein incorporated by reference. These and other cutting methods may also include saw cutting (e.g., diamond grit embedded semiconductor dicing blade), etching (for example using the etching process described in U.S. Pat. No. 5,106,455, the entire disclosure of which is herein incorporated by reference), laser cutting, electron discharge machining, or the like. It should be noted that the methods for manufacturing guidewire 10 may include forming slots 26 in tubular member 24 using any of these or other manufacturing steps.

Various embodiments of arrangements and configurations of slots 26 are contemplated. Slots 26 may be generally arranged to be perpendicular to the longitudinal axis of tubular member 24. This arrangement can, alternatively, be described as having slots 26 lying within a plane that is normal to the longitudinal axis of tubular member 24. In other embodiments, slots 26 may be formed at an angle relative to a plane that is normal to the longitudinal axis. In some embodiments, slots 26 may be formed part way through tubular member 24, while in other embodiments, slots 26 may extend all the way through tubular member 24. Any one or more of the individual slots 26 may extend only partially around the longitudinal axis of tubular member 24. In yet other embodiments, slots 26 may extend in a helical arrangement about the longitudinal axis of tubular member 24. Slots 26 may be formed in groups of two, three, or more slots 26, which may be located at substantially the same location along the axis of tubular member 24, and may be substantially perpendicular to the longitudinal axis. The distribution and/or configuration of slots 24 can also include, to the extent applicable, any of those disclosed in U.S. Pat. Publication No. US 2004/0181174 A2, the entire disclosure of which is herein incorporated by reference.

Figure 3:
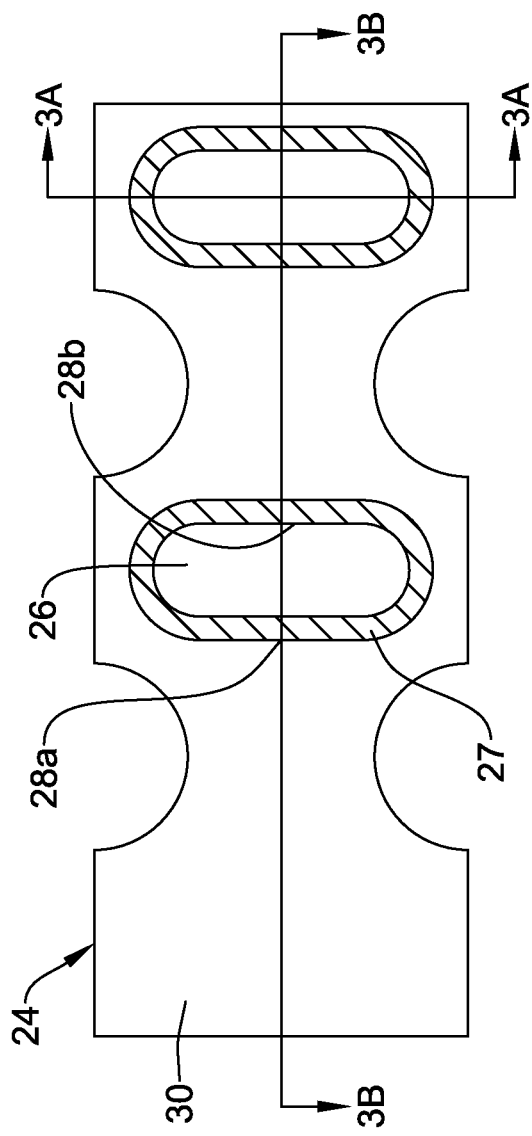
FIG. 3 illustrates a portion of an example tubular member.

Slots 26 may be disposed in tubular member 24 with at least some of these design considerations in mind. Turning now to FIG. 3, which shows a portion of tubular member 24, here it can be seen that slots 26 may have an oval or elliptical shape. In addition to having this shape, slots 26 may also be formed in tubular member 24 in a manner such that slots 26 have a different geometry or shape at the outside surface 30 of tubular member 24 than at the inside surface 31 (best seen in FIG. 3A) of tubular member 24. For example, slots 26 may have a first geometry or shape 28a along the outer surface 30 and a second geometry or shape 28b along the inner surface 31. It should be noted that numerous geometries/shapes are contemplated outside of what is shown, including circles, triangles, squares, rectangles, parallelograms, rhombuses, trapezoids, polygons (including polygons having essentially any number of sides), regular-shaped objects, irregularly shaped objects, star shapes, letter shapes (e.g., "U" shaped, "L" shaped, etc.), or any other suitable shape.

In some embodiments, first geometry 28a and second geometry 28b are different sizes of the same shape. Thus, first geometry 28a and second geometry 28b are geometrically similar—i.e., are different sizes of the same shape. This may be true even if the curves or arcs that formed the oval, ellipse, or other closed figure are different due to the different sizes of the objects. The intention is that the geometry of slots 26 is different between outer surface 30 and inner surface 31 in at least some tangible way including, for example, a change in size and/or a change in shape. This notation, however, is not intended to mean that geometries 28a/28b are necessarily different geometric forms (e.g., circle versus square) even though these types of arrangements are contemplated. Thus, some embodiments of tubular members 24 include slots 26 that have a different shape altogether (e.g., circle versus square) along outer surface 30 than along inner surface 31.

Figure 3A:
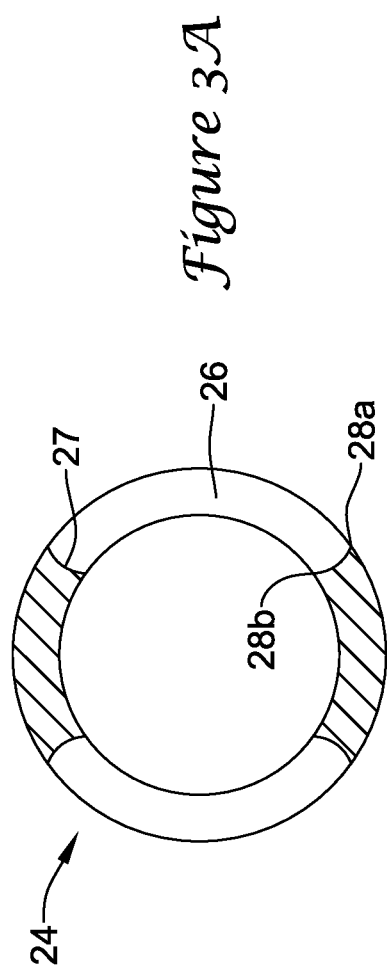
FIG. 3A is a cross-sectional view of the tubular member depicted in FIG. 3.
Figure 3B:
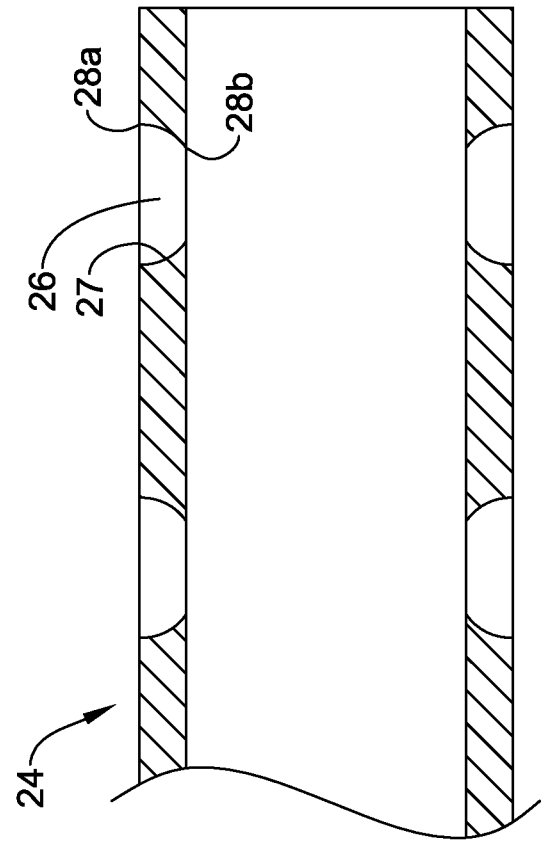
FIG. 3B is an alternate cross-sectional view of the tubular member depicted in FIG. 3.

Between the outer and inner surfaces 30/31, tubular member 24 may include a bevel or beveled region 27 where the first geometry 28a transitions to the second geometry 28b (see also FIGS. 3A-3B). Bevel 27 may be disposed at essentially any suitable angle relative to outer surface 30. In addition, bevel 27 may be disposed at a constant angle, a changing or variable angle, in a stepwise manner, and the like, or in any suitable fashion. Thus, bevel 27 may be a structural element of tubular member 24 where first geometry 28*a* changes to second geometry 28*b*.

Forming slots 26 may include the use of a suitable cutting device that includes a blade 32. Blade 32 includes a cutting surface 34 that is designed to create the desired shape and/or configuration for slots 26. For example, blade 32 may include a rounded or curved cutting surface 34 that can form the oval slots 26 in tubular member 24. In addition, the arced shape of cutting surface 34 may also be configured to form bevel 27.

In can be appreciated that blade 32 may form slots 26 such that the width of slot 26 along inner surface 31 is smaller than the width of slot 26 along outer surface 30. This may provide tubular member 24 with a number of desirable features. For example, some slot 26 geometries and/or configurations may provide better fatigue life versus stiffness, better axial stiffness versus bending stiffness ratios, better torsional versus bending stiffness ratios, etc. than other slot shapes and/or configurations. In addition, the geometry and/or configuration of slots 26 may be chosen to reduce machining and/or cutting time by reducing the number of features incorporated into tubular member 24 per unit length. For example, because slots 26 may be wider along outer surface 30, fewer slots 26 may be needed to produce a tubular member 24 having the desired properties (e.g., flexibility, torsional rigidity, etc.). In at least some embodiments, blade 32 can form slots 26 so that they have a width along outer surface 30 that is has about one tenth or more of the length of the outer diameter of tubular member 24. Conversely, the width of slots 26 along inner surface 31 may be about one tenth or less of the length of the outer diameter of tubular member 24.

As described above in relation to FIG. 3, slots 26 may be oval. However, the depiction of slots 26 as being oval is not intended to be limiting as several other shapes are contemplated. For example, FIG. 5 illustrates a portion of tubular member 124 having slots 126 with a half-moon shape. It should be noted that the phrase "half-moon" shape may termed crescent shaped, semi-circular, semi-oval, etc. without departing from the spirit of the invention. Just like slots 26, because of bevel 127, slots 126 have first geometry or shape 128*a* along the outer surface 130 of tubular member 124 and second geometry or shape 128*b* along the inner surface. Forming slots 126 may include the use of blade 132 having cutting surface 134. Cutting surface 134 may have a wedge-like shape or appearance.

Figure 7:
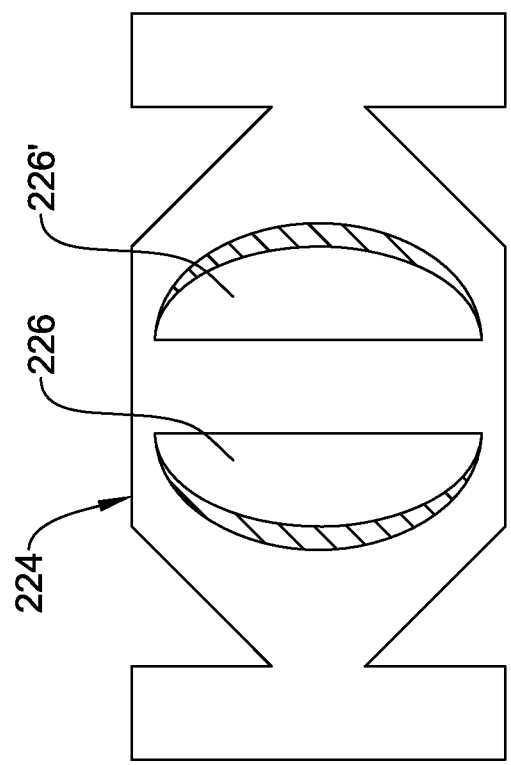
FIG. 7 illustrates a portion of another example tubular member.

The arrangement of slots 126 can also vary. For example, FIG. 5 illustrates that slots 126 may be sequentially disposed along the longitudinally axis of tubular member 124. For example, a series of slots (e.g., a first slot 126 and a second slot 126') are sequentially disposed such that arched portions of slots 126/126' are on the same side. FIG. 7 illustrates another example tubular member 224 where subsequent slots (e.g., a first slots 226 and a second slot 226') are reverse such that the arched portions of slots 226/126' are on opposite sides.

A portion of another example tubular member 324 is shown in FIG. 8. Tubular member 324 includes slots 326 that are diamond shaped. Slots 326 include bevel 327 that dictates that slots 326 have first geometry or shape 328*a* at the outer surface 330 of tubular member 324 and second geometry or shape 328*b* at the inner surface. Forming slots 326 may include the use of blade 332 having cutting surface 334. Cutting surface 334 may have a pointed shape, for example.

The materials that can be used for the various components of guidewire 10 may include those commonly associated with medical devices. It should be noted that any discussion related to a particular core wire (e.g., core wire 18), tubular member (e.g., tubular member 24), sheath (e.g., sheath 22), or any other component of a guidewire (e.g., guidewire 10) may also hold true for other core wires, tubular members, etc. disclosed herein. For example, core wire 18 and/or tubular member 24 (and/or other core wires, tubular members, etc. disclosed herein) may be made from a metal, metal alloy, a metal-polymer composite, combinations thereof, and the like, or any other suitable material. Some examples of suitable metals and metal alloys include stainless steel, such as 304V, 304L, and 316LV stainless steel; mild steel; nickel-titanium alloy such as linear-elastic and/or super-elastic nitinol; other nickel alloys such as nickel-chromium-molybdenum alloys (e.g., UNS: N06625 such as INCONEL® 625, UNS: N06022 such as HASTELLOY® C-22®, UNS: N10276 such as HASTELLOY® C276®, other HASTELLOY® alloys, and the like), nickel-copper alloys (e.g., UNS: N04400 such as MONEL® 400, NICKELVAC® 400, NICORROS® 400, and the like), nickel-cobalt-chromium-molybdenum alloys (e.g., UNS: R30035 such as MP35-N® and the like), nickel-molybdenum alloys (e.g., UNS: N10665 such as HASTELLOY® ALLOY B2®), other nickel-chromium alloys, other nickel-molybdenum alloys, other nickel-cobalt alloys, other nickel-iron alloys, other nickel-copper alloys, other nickel-tungsten or tungsten alloys, and the like; cobalt-chromium alloys; cobalt-chromium-molybdenum alloys (e.g., UNS: R30003 such as ELGILOY®, PHYNOX®, and the like); platinum enriched stainless steel; combinations thereof; and the like; or any other suitable material.

As alluded to above, within the family of commercially available nickel-titanium or nitinol alloys, is a category designated "linear elastic" or "non-super-elastic" which, although may be similar in chemistry to conventional shape memory and super elastic varieties, may exhibit distinct and useful mechanical properties. Linear elastic and/or non-super-elastic nitinol may be distinguished from super elastic nitinol in that the linear elastic and/or non-super-elastic nitinol does not display a substantial "superelastic plateau" or "flag region" in its stress/strain curve like super elastic nitinol does. Instead, in the linear elastic and/or non-super-elastic nitinol, as recoverable strain increases, the stress continues to increase in a substantially linear, or a somewhat, but not necessarily entirely linear relationship until plastic deformation begins or at least in a relationship that is more linear that the super elastic plateau and/or flag region that may be seen with super elastic nitinol. Thus, for the purposes of this disclosure linear elastic and/or non-super-elastic nitinol may also be termed "substantially" linear elastic and/or non-super-elastic nitinol.

In some cases, linear elastic and/or non-super-elastic nitinol may also be distinguishable from super elastic nitinol in that linear elastic and/or non-super-elastic nitinol may accept up to about 2-5% strain while remaining substantially elastic (e.g., before plastically deforming) whereas super elastic nitinol may accept up to about 8% strain before plastically deforming. Both of these materials can be distinguished from other linear elastic materials such as stainless steel (that can also can be distinguished based on its composition), which may accept only about 0.2-0.44% strain before plastically deforming.

In some embodiments, the linear elastic and/or non-super-elastic nickel-titanium alloy is an alloy that does not show any martensite/austenite phase changes that are detectable by DSC and DMTA analysis over a large temperature range. For example, in some embodiments, there may be no martensite/austenite phase changes detectable by DSC and DMTA analysis in the range of about −60° C. to about 120° C. in the linear elastic and/or non-super-elastic nickel-titanium alloy.

The mechanical bending properties of such material may therefore be generally inert to the effect of temperature over this very broad range of temperature. In some embodiments, the mechanical bending properties of the linear elastic and/or non-super-elastic nickel-titanium alloy at ambient or room temperature are substantially the same as the mechanical properties at body temperature, for example, in that they do not display a super-elastic plateau and/or flag region. In other words, across a broad temperature range, the linear elastic and/or non-super-elastic nickel-titanium alloy maintains its linear elastic and/or non-super-elastic characteristics and/or properties and has essentially no yield point.

In some embodiments, the linear elastic and/or non-super-elastic nickel-titanium alloy may be in the range of about 50 to about 60 weight percent nickel, with the remainder being essentially titanium. In some embodiments, the composition is in the range of about 54 to about 57 weight percent nickel. One example of a suitable nickel-titanium alloy is FHP-NT alloy commercially available from Furukawa Techno Material Co. of Kanagawa, Japan. Some examples of nickel titanium alloys are disclosed in U.S. Pat. Nos. 5,238,004 and 6,508,803, which are incorporated herein by reference. Other suitable materials may include ULTANIUM™ (available from Neo-Metrics) and GUM METAL™ (available from Toyota). In some other embodiments, a superelastic alloy, for example a superelastic nitinol can be used to achieve desired properties.

In at least some embodiments, portions or all of core wire 18 and/or tubular member 24 (and/or other core wires, tubular members, etc. disclosed herein) may also be doped with, made of, or otherwise include a radiopaque material. Radiopaque materials are understood to be materials capable of producing a relatively bright image on a fluoroscopy screen or another imaging technique during a medical procedure. This relatively bright image aids the user of device 10 in determining its location. Some examples of radiopaque materials can include, but are not limited to, gold, platinum, palladium, tantalum, tungsten alloy, polymer material loaded with a radiopaque filler, and the like. Additionally, radiopaque marker bands and/or coils may be incorporated into the design of guidewire 10 to achieve the same result.

In some embodiments, a degree of MRI compatibility is imparted into device 10. For example, to enhance compatibility with Magnetic Resonance Imaging (MRI) machines, it may be desirable to make core wire 18 and/or tubular member 24, or other portions of the medical device 10, in a manner that would impart a degree of MRI compatibility. For example, core wire 18 and/or tubular member 24, or portions thereof, may be made of a material that does not substantially distort the image and create substantial artifacts (artifacts are gaps in the image). Certain ferromagnetic materials, for example, may not be suitable because they may create artifacts in an MRI image. Core wire 18 and/or tubular member 24, or portions thereof, may also be made from a material that the MRI machine can image. Some materials that exhibit these characteristics include, for example, tungsten, cobalt-chromium-molybdenum alloys (e.g., UNS: R30003 such as ELGILOY®, PHYNOX®, and the like), nickel-cobalt-chromium-molybdenum alloys (e.g., UNS: R30035 such as MP35-N® and the like), nitinol, and the like, and others.

Referring now to core wire 18, the entire core wire 18 can be made of the same material along its length, or in some embodiments, can include portions or sections made of different materials. In some embodiments, the material used to construct core wire 18 is chosen to impart varying flexibility and stiffness characteristics to different portions of core wire 18. For example, the proximal region and the distal region of core wire 18 may be formed of different materials, for example materials having different moduli of elasticity, resulting in a difference in flexibility. In some embodiments, the material used to construct the proximal region can be relatively stiff for pushability and torqueability, and the material used to construct the distal region can be relatively flexible by comparison for better lateral trackability and steerability. For example, the proximal region can be formed of straightened 304v stainless steel wire or ribbon and the distal region can be formed of a straightened super elastic or linear elastic alloy, for example a nickel-titanium alloy wire or ribbon.

In embodiments where different portions of core wire 18 are made of different materials, the different portions can be connected using any suitable connecting techniques. For example, the different portions of core wire 18 can be connected using welding (including laser welding), soldering, brazing, adhesive, or the like, or combinations thereof. Additionally, some embodiments can include one or more mechanical connectors or connector assemblies to connect the different portions of core wire 18 that are made of different materials. The connector may include any structure generally suitable for connecting portions of a guidewire. One example of a suitable structure includes a structure such as a hypotube or a coiled wire which has an inside diameter sized appropriately to receive and connect to the ends of the proximal portion and the distal portion. Some other examples of suitable techniques and structures that can be used to interconnect different shaft sections are disclosed in U.S. patent application Ser. No. 09/972,276 filed on Oct. 5, 2001, now U.S. Pat. No. 6,918,882; Ser. No. 10/068,992 filed on Feb. 28, 2002; and Ser. No. 10/375,766 filed on Feb. 26, 2003, published as U.S. Publication No. 2004/0167441, which are incorporated herein by reference.

Core wire 18 can have a solid cross-section, but in some embodiments, can have a hollow cross-section. In yet other embodiments, core wire 18 can include a combination of areas having solid cross-sections and hollow cross sections. Moreover, core wire 18, or portions thereof, can be made of rounded wire, flattened ribbon, or other such structures having various cross-sectional geometries. The cross-sectional geometries along the length of core wire 18 can also be constant or can vary. For example, FIG. 2 depicts core wire 18 as having a round cross-sectional shape. It can be appreciated that other cross-sectional shapes or combinations of shapes may be utilized without departing from the spirit of the invention. For example, the cross-sectional shape of core wire 18 may be oval, rectangular, square, polygonal, and the like, or any suitable shape.

Sheath 22 may be made from a polymer or any other suitable material. Some examples of suitable polymers may include polytetrafluoroethylene (PTFE), ethylene tetrafluoroethylene (ETFE), fluorinated ethylene propylene (FEP), polyoxymethylene (POM, for example, DELRIN® available from DuPont), polyether block ester, polyurethane, polypropylene (PP), polyvinylchloride (PVC), polyether-ester (for example, ARNITEL® available from DSM Engineering Plastics), ether or ester based copolymers (for example, butylene/poly(alkylene ether) phthalate and/or other polyester elastomers such as HYTREL® available from DuPont), polyamide (for example, DURETHAN® available from Bayer or CRISTAMID® available from Elf Atochem), elastomeric polyamides, block polyamide/ethers, polyether block amide (PEBA, for example available under the trade name PEBAX®), ethylene vinyl acetate copolymers (EVA), silicones, polyethylene (PE), Marlex high-density polyethylene, Marlex low-density polyethylene, linear low density polyethylene (for example REXELL®), polyester, polybutylene terephthalate (PBT), polyethylene terephthalate (PET), polytrimethylene terephthalate, polyethylene naphthalate (PEN), polyetheretherketone (PEEK), polyimide (PI), polyetherimide (PEI), polyphenylene sulfide (PPS), polyphenylene oxide (PPO), poly paraphenylene terephthalamide (for example, KEVLAR®), polysulfone, nylon, nylon-12 (such as GRILAMID® available from EMS American Grilon), perfluoro(propyl vinyl ether) (PFA), ethylene vinyl alcohol, polyolefin, polystyrene, epoxy, polyvinylidene chloride (PVdC), polycarbonates, ionomers, biocompatible polymers, other suitable materials, or mixtures, combinations, copolymers thereof, polymer/metal composites, and the like. In some embodiments sheath 22 can be blended with a liquid crystal polymer (LCP). For example, the mixture can contain up to about 6% LCP. This has been found to enhance torqueability. By employing selection of materials and processing techniques, thermoplastic, solvent soluble, and thermosetting variants of these and other materials can be employed to achieve the desired results.

In some embodiments, the exterior surface of the guidewire 10 (including, for example, the exterior surface of core wire 18 and/or the exterior surface of tubular member 24) may be sandblasted, beadblasted, sodium bicarbonate-blasted, electropolished, etc. In these as well as in some other embodiments, a coating, for example a lubricious, a hydrophilic, a protective, or other type of coating may be applied over portions or all of sheath 22, or in embodiments without a sheath 22 over portion of core wire 18 and/or tubular member, or other portions of device 10. Alternatively, sheath 22 may comprise a lubricious, hydrophilic, protective, or other type of coating. Hydrophobic coatings such as fluoropolymers provide a dry lubricity which improves guidewire handling and device exchanges. Lubricious coatings improve steerability and improve lesion crossing capability. Suitable lubricious polymers are well known in the art and may include silicone and the like, hydrophilic polymers such as highdensity polyethylene (HDPE), polytetrafluoroethylene (PTFE), polyarylene oxides, polyvinylpyrolidones, polyvinylalcohols, hydroxy alkyl cellulosics, algins, saccharides, caprolactones, and the like, and mixtures and combinations thereof. Hydrophilic polymers may be blended among themselves or with formulated amounts of water insoluble compounds (including some polymers) to yield coatings with suitable lubricity, bonding, and solubility. Some other examples of such coatings and materials and methods used to create such coatings can be found in U.S. Pat. Nos. 6,139,510 and 5,772,609, which are incorporated herein by reference.

The coating and/or sheath 22 may be formed, for example, by coating, extrusion, co-extrusion, interrupted layer co-extrusion (ILC), or fusing several segments end-to-end. The layer may have a uniform stiffness or a gradual reduction in stiffness from the proximal end to the distal end thereof. The gradual reduction in stiffness may be continuous as by ILC or may be stepped as by fusing together separate extruded tubular segments. The outer layer may be impregnated with a radiopaque filler material to facilitate radiographic visualization. Those skilled in the art will recognize that these materials can vary widely without deviating from the scope of the present invention.

FIGS. 10-20 depict a variety of example tubular members and cuts formed in the example tubular members in order to illustrate some addition variations contemplated for the distribution of slots in a tubular member. For convenience, similar reference numbers are used throughout these figures. However, several different tubular member may be formed or defined according to the forgoing description including several that may be utilized in any of the devices and/or guidewire disclosed herein. The description of these figures make use of the words "beam" and/or "beams". The beams are the portion of the tubular member, often resembling a beam in appearance, that remains after cutting away a portion of the tubular member to form the slots.

Figure 10:
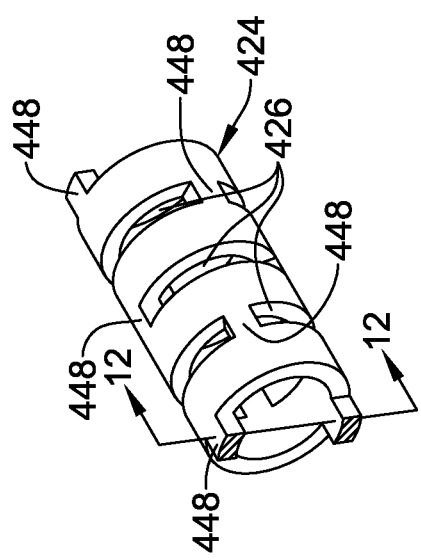
FIG. 10 is a perspective view of a portion of another example tubular member.
Figure 11:
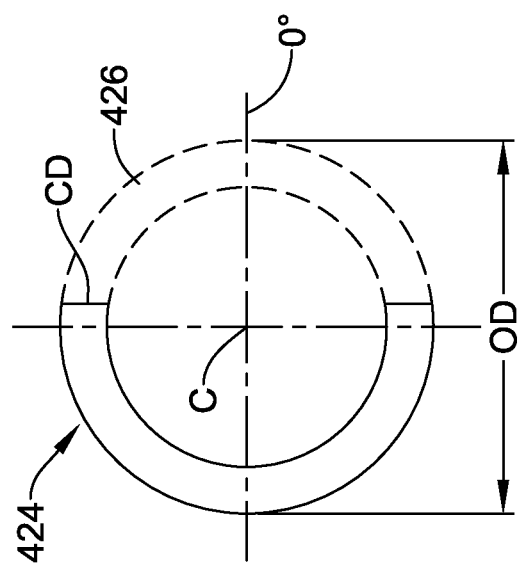
FIG. 11 is a cross-sectional view depicting an example tubular member and cuts that can be utilized to form slots in the tubular member.

Turning now to FIG. 10, which is a perspective view of an example tubular member 424, here it can be generally seen how slots 426 may be distributed along tubular member 424 as well as how beams 428 are located between slots 426. Turning now to FIG. 11, when a cutting member or blade cuts into tubular member 424 to form slots, the blade slice through tubular member 424 at a particular angular position (e.g., for convenience sake assume the angular position is located at the right hand side or the 0° position of tubular member 424) to a position called the cut depth CD and defines a slot 426 (depicted in phantom as the portion of tubular member 424 removed by cutting). In this example, the beam height BH is the length of width of the beam in the radial direction. The beam height BH may be related to the cut depth CD and the outer diameter OD of tubular member 424. For example, in at least some cases the "deeper" the cut depth CD, the "shorter" the beam height BH. In fact, the relationship between cut depth CD and beam height BH can be represented by the equation:

$$CD=0.5*(OD-BH)$$

Figure 12:
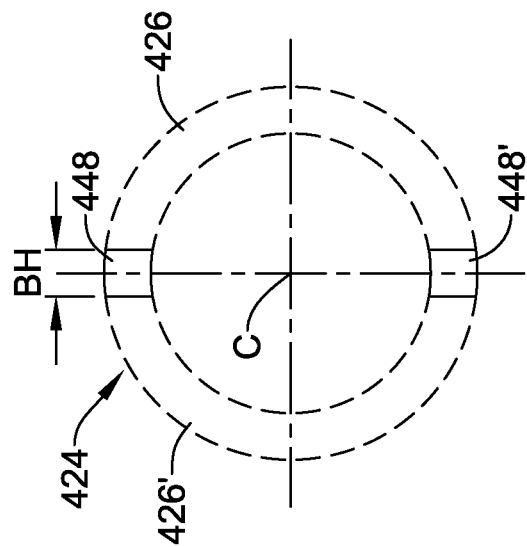
FIG. 12 is a cross-sectional view taken through line 12-12 in FIG. 10.

Another cut may be made in tubular member 424 at the same longitudinal position (e.g., from the opposite angular position (e.g., 180°) of tubular member 424 as shown in FIG. 12. Here it can be seen that a second slot 426' is formed. Not only does the second cut form a pair of slots 426/426', a pair of beams 448/448' are defined.

Figure 13:
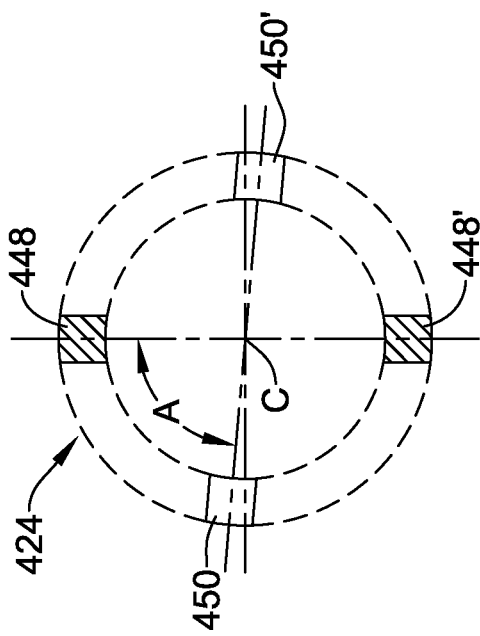

Along the length of tubular member 424, additional pairs of slots and beams can be formed by making additional cuts. In some embodiments, the cuts can be from the same position (e.g., from the 0° and the 180° positions of tubular member 424). Alternatively, the cuts can begin from a different angular position. For example, the first cut made in tubular member 424 at a subsequent longitudinal position may be rotated a radial distance or angle A from where the first cut was made at the first longitudinal position. Angle A could be any suitable angle such as, for example, about 60-120° or about 85° as shown in FIG. 13. Another cut from the opposite side of tubular member 424 defines a second pair of beams 450/450'. At other longitudinal positions, cuts can be rotated to the same extent or to different extents.

Figure 14:
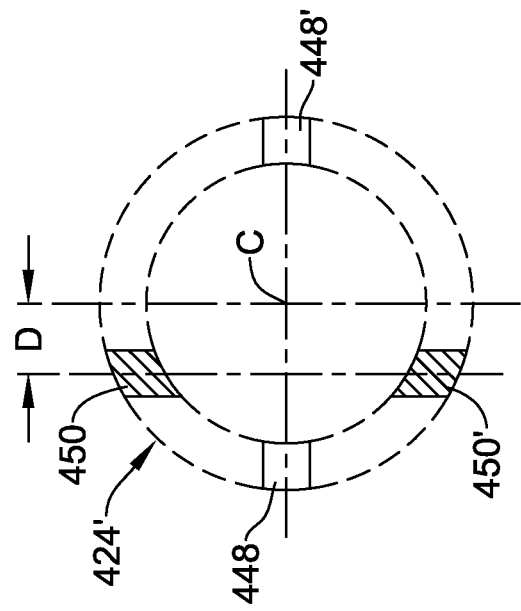
FIGS. 13-20 are cross-sectional views depicting example tubular members and various cuts that can be utilized to form slots in the tubular members.

It can be appreciated that all the beam pairs 448/448' and/or 450/450' all have centers that align with the tube centerline C (i.e., a line drawn between the middle of opposing pairs of beams goes through the tube centerline C). While this can be desirable in some embodiments, other arrangements are contemplated that include beam centers that are offset from the tube centerline C to create structures with lower bending stiffness. For example, FIG. 14 depicts tubular member 424' where beam pairs 448/448' and beam pairs 450/450' are rotated 90° relative to one another. Beams 448/448' are aligned with the tube centerline C. However, beams 450/450' are offset a distance D from the tube centerline C. Arrangements like this may result in a tubular member that is anisotrophic (i.e., soft in bending in one plane relative to other planes). Other arrangements are contemplated where both beams 448/448' and beams 450/450' are offset from the tube centerline C. The amount of offset may or may not be the same. In addition, the beam pairs may or may not be rotated around the circumference of tubular member 424' at any suitable angle. Embodiments where the offsets are the same and the angle is fixed may result in a tubular member that is isotrophic.

Figure 15:
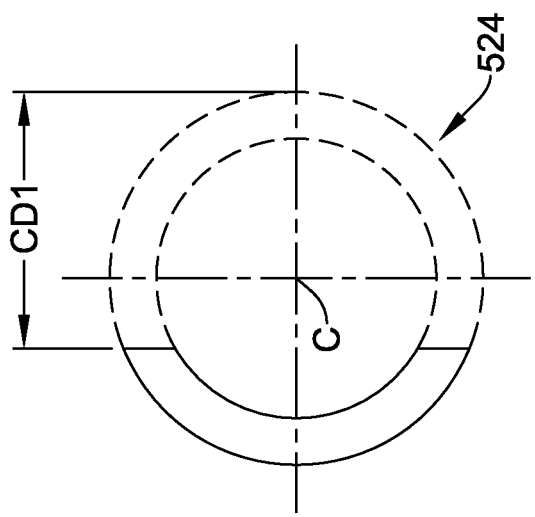

Additional variation are contemplated for other "offset" beam structures. Turning now to FIG. 15, the cross-section of another example tubular member 524 is shown that can be used in any of the device described herein. The structure of tubular member 524 includes a slot/beam arrangement wherein the amount or distance of the beam offset varies as a function of the angular position from which the cut defining the slot/beam originates from. To understand the arrangement contemplated, several relationships can be defined. For example, CD1 is the first cut in a pair of cuts that creates a pair of beams. CD2 is the second cut in a pair of cuts that creates a pair of beams. The MAXOFFSET is the maximum desired beam centerline offset, which can be fixed as any suitable distance. The ANGULARPOSITION is the angle from which the blade approaches the tube centerline C to make a given cut.

Using the traditional diagram associated with sine and cosine functions (a circle with 0° to the right of the origin, and the angular position increasing with counterclockwise rotation about the origin), the depth of any given cut (e.g., cut depth CDn or nominal cut depth) can be defined by a function of the ANGULARPOSITION, such as:

CD$n$=CD+MAXOFFSET*Cos(ANGULARPOSITION)

Cut depth CD is defined above. If the first cut is made from the 0° position:

CD1=CD+MAXOFFSET*Cos(0°)

Because the Cos(0°) is 1:

CD1=CD+MAXOFFSET

CD1 is depicted in FIG. 15. For the second cut, ANGULARPOSITION may be 180°, so:

CD2=CD+MAXOFFSET *Cos(180°)

Because the Cos(180°) is (−1):

CD2=CD−MAXOFFSET

Figure 16:
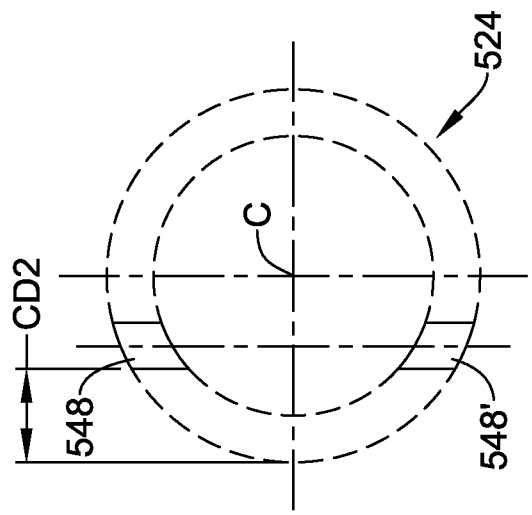

CD2 is depicted in FIG. 16. These two cuts then result in a pair of beams 548/548' whose centerline is shifted MAXOFFSET units from the tube centerline toward the 180° direction (to the left).

If subsequent pairs of cuts are rotated, for example, at an angle of 85° between cut pairs, the next cut in the sequence would approach the tube centerline from 265°. This "third" cut would have a cut depth CD3 that would be:

$$CD3 = CD + MAXOFFSET * Cos(265°)$$
$$= CD - .0872 * MAXOFFSET$$

Figure 17:
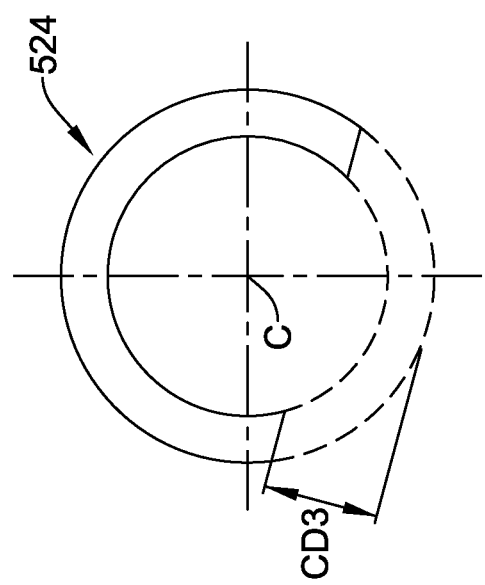

CD3 is depicted in FIG. 17. The next or "fourth" cut would approach from 265°+180° or 445° (or 445°−360°=85°) and have a cut depth CD4 that would be:

CD4=CD+0.0872*MAXOFFSET

Figure 18:
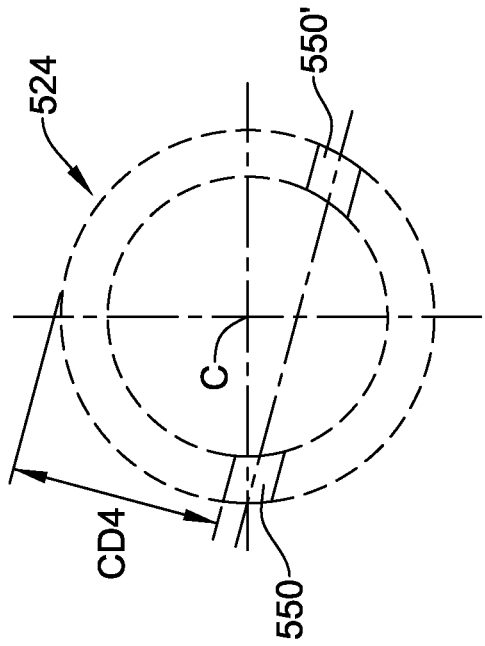

CD4 is depicted in FIG. 18. The beam centerline for this pair of beams 550/550' would be 0.0872*MAXOFFSET units from the tube centerline C, toward the 265° position. The next cut would come from 85° (position of last cut)+85° (helix angle) or 170°. Thus, the "fifth" cut would have a fifth cut depth CD5 that would be:

CD5=CD−0.9848*MAXOFFSET

Figure 19:
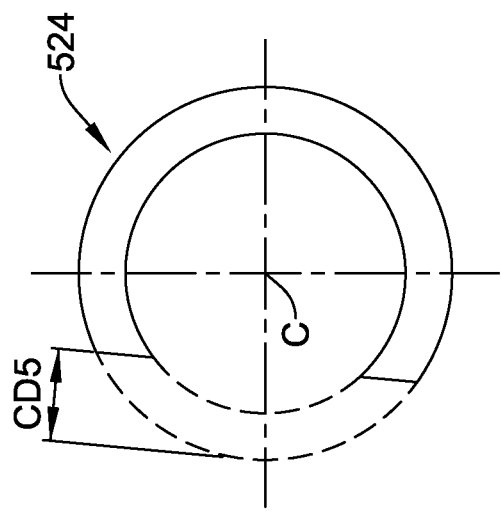

CD5 is depicted in FIG. 19. The next cut would come from 170°+180° or 350°. Thus, the "sixth" cut would have a sixth cut depth CD6 that would be:

CD6=CD+0.9849*MAXOFFSET

Figure 20:
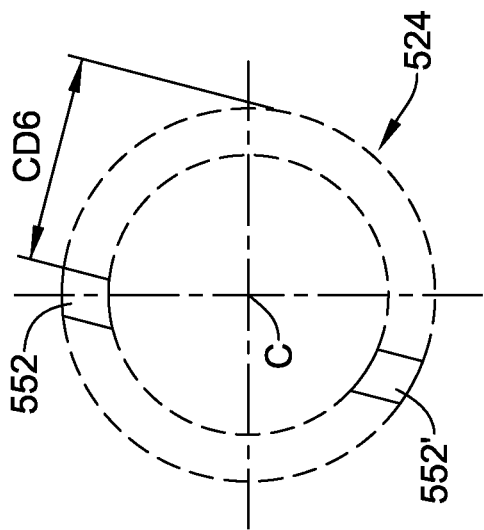

CD6 is depicted in FIG. 20. The beam centerline for this pair of beams 552/552' would be shifted 0.9848*MAXOFFSET units from the tube centerline, toward the 170° direction.

This function will place the beam centerlines for all vertical beam pairs MAXOFFSET units to the left of the tube centerline (Cos 0°=1, Cos 180°=−1), and the beam centerlines for all horizontal beam pairs directly on the tube centerline (Cos 90°=Cos 270°=0). The beam-tube centerline offset for beam pairs at other angles will be distributed via the Cosine function between 0 and MAXOFFSET units. It can be appreciated that a similar strategy can be utilized using different functions (e.g., Sine, Tangent, etc.)

It should be understood that this disclosure is, in many respects, only illustrative. Changes may be made in details, particularly in matters of shape, size, and arrangement of steps without exceeding the scope of the invention. The invention's scope is, of course, defined in the language in which the appended claims are expressed.

What is claimed is:
1. A medical device, comprising:
   a core member having a proximal region and a distal region;
   a tubular member disposed over the distal region of the core member;
   wherein the tubular member has a length and a plurality of slots defined through a side wall of the tubular member, the plurality of slots including a plurality of opposed pairs of slots, each opposed pair of slots comprising a first slot at an axial position on the tubular member and a second slot at the same axial position on the tubular member;
   a plurality of pairs of beams, each pair of beams including a first beam disposed between a first end of the first slot and a first end of the second slot, and a second beam disposed between a second end of the first slot and a second end of the second slot;
   wherein at least some of the pairs of beams are offset from a central axis of the tubular member by a distance from the central axis to a plane passing through each of the beams in the pair of beams parallel to the central axis;
   wherein the distance from the central axis to the plane oscillates along the length of the tubular member;
   wherein the distance from the central axis to the plane oscillates in accordance with a cosine function; and
   wherein the distance that the pairs of beams are offset from the central axis is defined by:

CD$_2$=CD$_1$+MAXOFFSET* Cos(ANGULAR POSITION); where

CD$_1$ is a depth of a first cut in the tubular member,
   CD$_2$ is a depth of a second cut in the tubular member,
   MAXOFFSET is the distance that the beams are offset from the central axis, and
   ANGULAR POSITION is an angle from which a cutting member approaches the central axis of the tubular member to make the second cut.
2. The medical device of claim 1, wherein the core member has a solid cross-section.
3. The medical device of claim 1, wherein the tubular member has an outer surface with a coating.

4. The medical device of claim 1, wherein only some of the pairs of beams are offset from the central axis of the tubular member.

5. The medical device of claim 1, wherein all of the pairs of beams are offset from the central axis of the tubular member.

6. The medical device of claim 1, wherein the first cut and the second cut are opposed cuts that define a first pair of beams.

7. The medical device of claim 6, wherein a second pair of beams are formed in the tubular member, the second pair of beams disposed at a position that is radially offset from the first pair of beams.

8. The medical device of claim 7, wherein one or more additional pairs of beams are formed in the tubular member that are disposed at positions that are radially offset from the first pair of beams, the second pair of beams, or both.

9. The medical device of claim 1, wherein the tubular member includes a nickel-titanium alloy.

* * * * *